United States Patent [19]

Johnson

[11] Patent Number: 4,505,093
[45] Date of Patent: Mar. 19, 1985

[54] APPARATUS FOR COLLATING ARTICLES TO BE WRAPPED INTO BATCHES

[75] Inventor: Reginald F. Johnson, Lea, near Gainsborough, England

[73] Assignee: Baker Perkins Holdings PLC, Peterborough, England

[21] Appl. No.: 368,351

[22] Filed: Apr. 14, 1982

[30] Foreign Application Priority Data

May 14, 1981 [GB] United Kingdom ............ 8114733

[51] Int. Cl.$^3$ .............................................. B65B 35/44
[52] U.S. Cl. .................................. 53/531; 53/225; 53/537; 53/540; 53/542; 198/732
[58] Field of Search .............. 53/531, 543, 537, 147, 53/228, 230, 234, 542, 533, 544, 225, 540; 198/425, 732

[56] References Cited

U.S. PATENT DOCUMENTS

| | | | |
|---|---|---|---|
| 2,090,928 | 8/1937 | Aisher | 198/732 |
| 3,253,387 | 5/1966 | Schmermund | 53/234 |
| 3,876,062 | 4/1975 | Honda | 198/732 |
| 3,902,587 | 9/1975 | Checcucci | 53/537 X |
| 3,927,508 | 12/1975 | Campbell | 53/542 X |
| 4,186,544 | 2/1980 | Johnson | 53/234 X |

*Primary Examiner*—Horace M. Culver
*Attorney, Agent, or Firm*—Watson, Cole, Grindle & Watson

[57] ABSTRACT

A packaging machine comprises a primary wrapper for applying wrappers to individual sweets, a collating mechanism for collating the wrapped sweets into batches and a batch wrapper for overwrapping the batches of sweets. Batching is effected by pushers on a chain conveyor which advance the sweets successively, along a support, the pushers normally tilting to disengage the sweets but the disengagement of every $n^{th}$ pusher with its sweet being delayed, where n is the number of sweets required in a batch. The machine can be readily modified to collate the sweets into batches in which the sweets lie flat or in an erect condition as desired.

5 Claims, 6 Drawing Figures

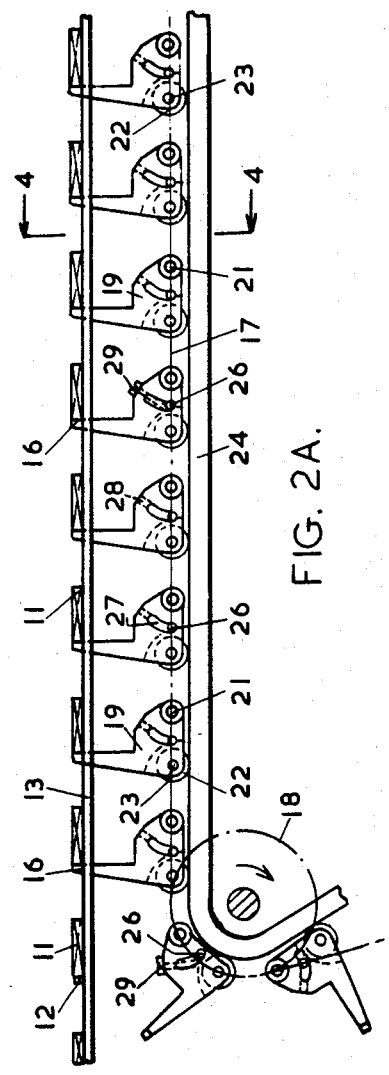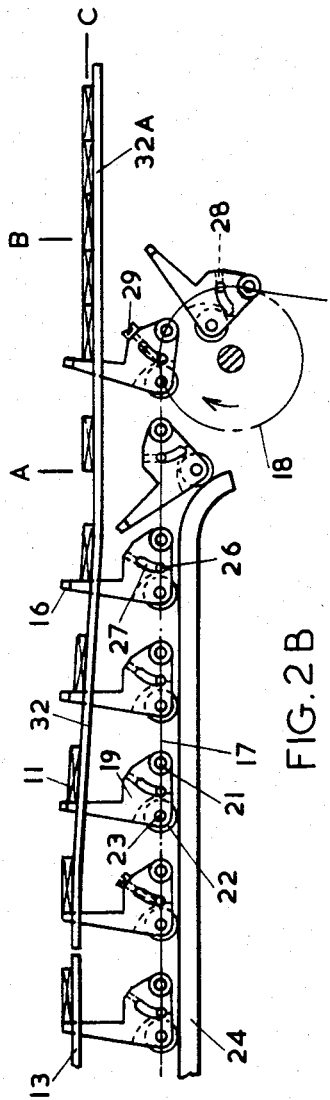
FIG. 2A.
FIG. 2B.

APPARATUS FOR COLLATING ARTICLES TO BE WRAPPED INTO BATCHES

A well known type of packaging machine, known as a stick packaging machine, includes a primary wrapper, which applies wrappers to individual sweets or like articles, a collating apparatus which collates the wrapped articles into batches, and a second wrapper which applies an overwrap to each batch of articles.

The present invention aims to provide, in such a packaging machine, a collating apparatus which collates the wrapped articles into batches in which the articles lie flat and end-to-end, which is readily convertible to a condition in which the wrapped articles in the batches stand erect and side-by-side, and which permits of ready adjustment of the number of wrapped articles in a batch.

The invention accordingly provides a packaging machine, comprising a primary wrapper for applying wrappers to individual sweets or like articles, a support having an initial substantially horizontal flat portion, a descending portion and a further substantially horizontal flat portion, means for feeding the wrapped articles in succession from a discharge point of the primary wrapper onto the support to form on the initial portion thereof a regularly spaced procession of articles in which the articles lie flat, a series of pushers engageable with the individual articles, means for moving the pushers to advance the articles along the support from its initial to its further portion, the pushers normally moving clear of the articles after they have reached the further portion of the support, means associated with every $n^{th}$ pusher of the series for preventing each such pusher from disengaging its associated article until said article had advanced, shunting $n-1$ articles in advance of it, to form a batch on the further portion of the support, an overwrapper constituted by a batch wrapping wheel rotatable about a horizontal axis aligned with the centre line of each batch of articles so formed and means for transferring said batches of articles laterally and in succession from the support to the batch wrapping wheel.

The support may have a gently inclined initial descending portion so that the articles remain flat in the collated batches. Alternatively the support may have a sufficiently sharply inclined descending portion to cause the articles to turn over into an erect attitude as they reach the further portion of the support. In each case the further flat portion is, of course, at the level appropriate for central presentation to the wrapping wheel of the flat or erect articles as the case may be. By modification of the descending and further portions of the support, which is conveniently made in two sections, the apparatus can therefore be easily modified to provide for collation of batches in which the articles are flat or erect as desired.

It is necessary for the support to have a descending portion, even when the articles are batched in the flat condition, and for the axis of rotation of the batch wrapping wheel to be at a lower level than the discharge point of the primary wrapper because there would otherwise be sufficient space for a sufficient drop in level of the descending portion of the support, when the articles are to be batched erect, to enable them to turn through 90°.

An embodiment of the invention is illustrated in the accompanying drawings in which:

FIG. 1 is a diagrammatic plan view of the complete machine;

FIGS. 2A and 2B, hereinafter referred to collectively as FIG. 2, are an elevation on a larger scale, showing that part of the machine which collates wrapped sweets in a condition to produce a flat over-wrapped pack;

Figure 1:
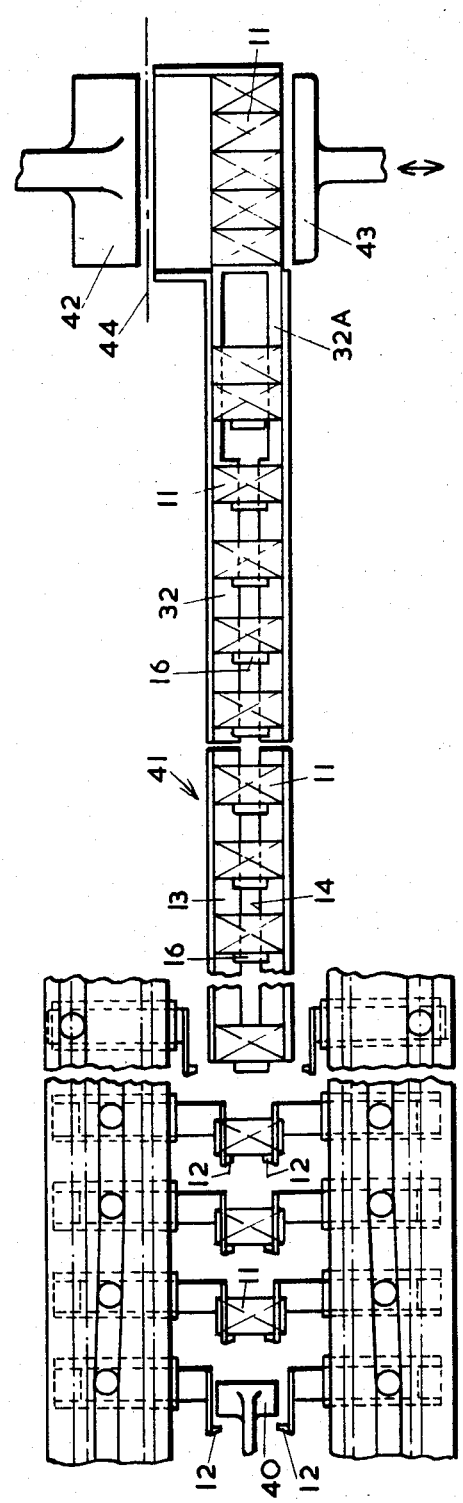

The machine shown in FIG. 1 consists essentially of a primary wrapper, constituted by an intermittently rotating wrapping wheel, one article-receiving pocket of which is shown at 40, a collating section 41, a batch wrapping wheel 42 which rotates intermittently about a horizontal axis, and a cross pusher 43 which transfers successive batches of wrapped articles to the wheel 42, each such batch carrying with it into the wheel 42 an overwrapper 44.

The apparatus illustrated is designed to collate batches of five wrapped sweets 11, each sweet having been wrapped in the primary wrapping wheel and removed therefrom, during a dwell in rotation thereof, by one of a series of pairs of co-operating fingers 12 which engage the rear faces of successive sweets 11, as described in the related and commonly owned U.S. Pat. No. 4,186,544. As shown in FIG. 2, the fingers 12 transfer the sweets onto a first horizontal support 13, provided with a longitudinal slot 14 through which successive pushers 16 travel. After the fingers 12 have moved the sweets clear of the primary wrapping wheel they are withdrawn and transport of the sweets along the support 13 is taken over by the pushers 16 which are carried by a chain conveyor consisting of a pair of continuously operating chains 17 mounted on sprockets 18. Each pusher 16 is constituted by a finger extending upwardly from a block 19 pivotally mounted at 21 on the chains 17. Rollers 22, mounted at 23 on the blocks 19, engage a cam track 24 extending between the sprockets 18, each roller 22 normally serving to maintain its pusher 16 in the upright position. Pegs 26, carried at intervals to the chains 17, engage arcuate slots 27 formed in the blocks 19. Each block 19 is provided with a threaded hole 28 which communicates with the upper end of its slot 27 and when, as illustrated, batches of five wrapped sweets are to be collated, a screw 29 is inserted in the hole 28 of every fifth block, the tip of the screw being in engagement with the peg 26.

The pushers 16 transport the sweets 11 along the support 13, between side guides 31, and then on to a second support having an initial downwardly sloping portion 32 and a following horizontal portion 32A. After the pusher 16 has moved the first sweet in a batch of five to point 'A', that pusher is allowed by the cam track 24 to pivot rearwardly out of contact with the sweet to leave it resting at that position until the next sweet in the batch approaches point 'A' whereupon that sweet shunts the first sweet along the portion 32 of the support and the pusher 16 of the second sweet is allowed to pivot rearwardly by the track 24. This action is repeated as the third and fourth sweets 11 of the batch arrive at point 'A'. When the fifth sweet arrives at this point, the screw 29 of its pusher 16 prevents its peg 26 moving in the slot 27. That pusher 16 cannot therefore pivot rearwardly and pushes the batch of five sweets 11 in advance of it along the support until the pusher travels around the sprocket 18 to depart from contact with the sweet in advance of it and leave the batch with the trailing edge of the fifth sweet at point 'B' on the horizontal portion 32A of the support. The batch is transferred from this position into a waiting pocket of the batch wrapping wheel 42 by the cross pusher 43 in known manner. The centre line 'C' of the sweets in the batch at this position is coincident with the axis of rotation of and therefore with the centre line of a pocket of the batch wrapping wheel 42.

Figure 3:
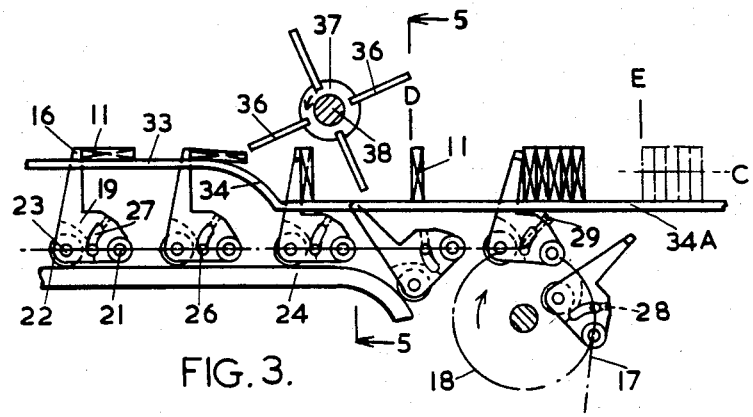
FIG. 3 is an elevation illustrating the apparatus shown in FIG. 2 modified to produce an on-edge overwrapped pack.
Figure 4:
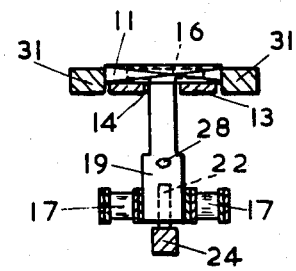
FIG. 4 is a section taken on the line 4—4 in FIG. 2.

When it is desired to collate batches of sweets 11 standing on edge, the second support 32 is replaced by a horizontal platform 33 having a curved secondary ramp 34 leading to a horizontal portion 34A as illustrated in FIG. 3. The sweets 11 are moved along the platform 33 in the flat state by the pushers 16 as before and, as each sweet passes down the ramp 34, it turns through 90° on to its edge. When the apparatus is running at a speed of 1000 sweets/minute, there is a tendency for the sweets 11 to overshoot the ramp 34 and hence turning of the sweets will not be effected. Accordingly, to ensure that the sweets 11 pass down the ramp 34, and to assist in the turning action of the sweets, one of a series of deflector blades 36 engages each sweet 11 during the time that the sweet travels down the ramp 34. The blades 36 are attached to a boss 37 secured to a continuously rotating shaft 38 driven at such a speed that, as the chains 17 advance the pushers 16 through one pitch distance, the blades 36 move through one quarter of a revolution of the shaft 38. The manner in which the blades 36 co-operate with the pushers 16 to ensure that, notwithstanding the high speed of advance of the sweets 11 each will be turned with certainty through 90° is more fully explained in the commonly owned and copending U.S. Ser. No. 368,320, filed on even data herewith.

Figure 5:
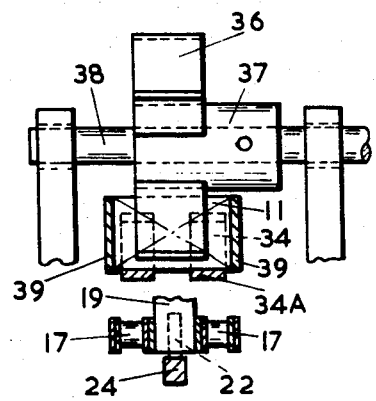
FIG. 5 is a section taken on the line 5—5 in FIG. 3.

When a pusher 16 has moved the first turned-over sweet 11 in a batch of five to point 'D', this pusher pivots rearwardly as described above to leave that sweet resting at that point. When the second, third and fourth sweets have been deposited at this position the fifth pusher 16, which carries a screw 29, moves the batch along the support to the point 'E', as shown in chain-dot lines, where the pusher 16 travels around the sprocket 18. From this position the batch is transferred as described above into a pocket of the batch wrapping wheel 42. Said batch wrapping wheel, like the wrapping wheel of the primary wrapper, is of conventional construction and the showing of a single pocket thereof is accordingly deemed sufficient. The portion 34A of the platform 33 is at such a level that again the centre line 'C' of the turned-over sweets 11 in a batch is coincident with the centre line of the pocket of the batch wrapping wheel 42. Side guides 39 (FIG. 5) support the erected sweets on the portion 34A of the platform until they reach the transfer position.

It will be appreciated from the foregoing description that it is a comparatively simple matter to modify the apparatus from the configuration illustrated in FIG. 2 which collates batches of sweets in the flat state to that illustrated in FIG. 3 for collating batches of sweets on edge.

Although the examples described and illustrated are applied to collating batches of five sweets, it will also be appreciated that the number of sweets in a batch may be readily varied by merely removing the screws 29 from every fifth block and inserting them in every $n^{th}$ block 19, where n is the number of sweets required in a batch.

I claim:

1. A packaging machine, comprising a primary wrapper for applying wrappers to individual sweets or like articles, a support having an initial substantially horizontal flat portion, a descending portion and a further substantially horizontal flat portion, means for feeding the wrapped articles in succession from a discharge point of the primary wrapper onto the support to form on the initial portion thereof a regularly spaced procession of articles in which the articles lie flat, a series of pushers which are disposed beyond said feeding means and are engageable, each with one of the articles, means for moving the pushers to advance the articles along the support from its initial to its further portion, the pushers normally moving clear of their respective articles after they have reached the further portion of the support to leave said articles resting in a stationary position, means associated with every $n^{th}$ pusher of the series for preventing each such pusher from disengaging its associated article until said article has advanced, shunting other articles in advance of it, to form with said other articles a batch of contacting articles on the further portion of the support, an overwrapper constituted by a batch wrapping wheel and means for transferring said batches of articles laterally and in succession from the support to the batch wrapping wheel.

2. A machine according to claim 1, in which the descending portion of the support is such that the articles remain flat in the collated batches.

3. A machine according to claim 1, in which the descending portion of the support is sufficiently sharply inclined to cause the articles to turn to an erect attitude as they reach the further portion of the support.

4. A machine according to claim 3, which includes a positively rotated bladed rotor which co-operates with the pushers during turning of the articles.

5. A packaging machine, comprising a primary wrapper for applying wrappers to individual sweets or like articles, a support having an initial substantially horizontal flat portion, a descending portion and a further substantially horizontal flat portion, means for feeding the wrapped articles in succession from a discharge point of the primary wrapper onto the support to form on the initial portion thereof a regularly spaced procession of articles in which the articles lie flat, a chain conveyor, a cam track, a series of pushers pivotably mounted on the chain conveyor and adapted to engage the individual articles on said support to advance them along the support, said cam track normally permitting said pushers to move about their pivots to clear the articles when they reach the further portion of said support, pegs on said conveyor which engage and move in slots in said pushers during said pivotal movement every $n^{th}$ pusher carrying a readily removable member preventing movement of the associated pegs in its slot so that said $n^{th}$ pusher is prevented from disengaging its associated article until said article has advanced, shunting other articles in advance of it, to form with said other articles a batch of contacting articles on the further portion of the support, an overwrapper constituted by a batch wrapping wheel and means for transferring said batches of articles laterally and in succession from the support to the batch wrapping wheel.

* * * * *